United States Patent
Willekens et al.

[11] Patent Number: 5,860,964
[45] Date of Patent: Jan. 19, 1999

[54] DIAPER FASTENING SYSTEM USING WELDED BRANCHING TYPE TABS

[75] Inventors: J. Willekens, Hoogstraten; J. Van de Water, Turnhout, both of Belgium; F. Coumans, Wouw, Netherlands; P. Dhondt, Vosselaar, Belgium

[73] Assignee: Avery Dennison Corporation, Painesville, Ohio

[21] Appl. No.: 853,639

[22] Filed: May 9, 1997

Related U.S. Application Data

[63] Continuation of Ser. No. 325,988, Oct. 19, 1994, abandoned.

[51] Int. Cl.$^6$ ....................................................... A61F 13/15
[52] U.S. Cl. ........................................... 604/389; 604/390
[58] Field of Search ..................................... 604/389, 390

[56] References Cited

U.S. PATENT DOCUMENTS

| | | | |
|---|---|---|---|
| 3,833,456 | 9/1974 | Reed et al. | |
| 3,848,594 | 11/1974 | Buell | |
| 3,920,016 | 11/1975 | Mesek et al. | 604/390 |
| 4,020,842 | 5/1977 | Richman et al. | |
| 4,378,800 | 4/1983 | Schaar | 604/390 |
| 4,726,871 | 2/1988 | Pape et al. | 604/390 |
| 4,795,456 | 1/1989 | Borgers et al. | 604/390 |
| 4,801,480 | 1/1989 | Panza et al. | 604/390 |
| 5,053,028 | 10/1991 | Zola et al. | 604/385.1 |
| 5,080,973 | 1/1992 | Nguyen | 604/390 |
| 5,085,655 | 2/1992 | Mann et al. | 604/390 |
| 5,147,347 | 9/1992 | Huang et al. | 604/390 |
| 5,176,670 | 1/1993 | Roessler et al. | 604/391 |
| 5,275,590 | 1/1994 | Huffman et al. | 604/390 |
| 5,288,546 | 2/1994 | Roessler et al. | 604/390 |

FOREIGN PATENT DOCUMENTS

3437167 A1  4/1986  Germany.

*Primary Examiner*—Randy C. Shay
*Attorney, Agent, or Firm*—Pearne, Gordon, McCoy & Granger LLP

[57] ABSTRACT

A diaper is provided with an adhesive fastening tab of the Y-configuration type which includes a welded joinder at the branching point between the fastening tape and release tape portions of the tab, the welded joinder being free of the diaper. The welded joinder comprises a direct weld between the substrates of the fastening tape and release tape portions of the tab, or welds between each of those two substrates and an intermediate junction substrate.

5 Claims, 3 Drawing Sheets

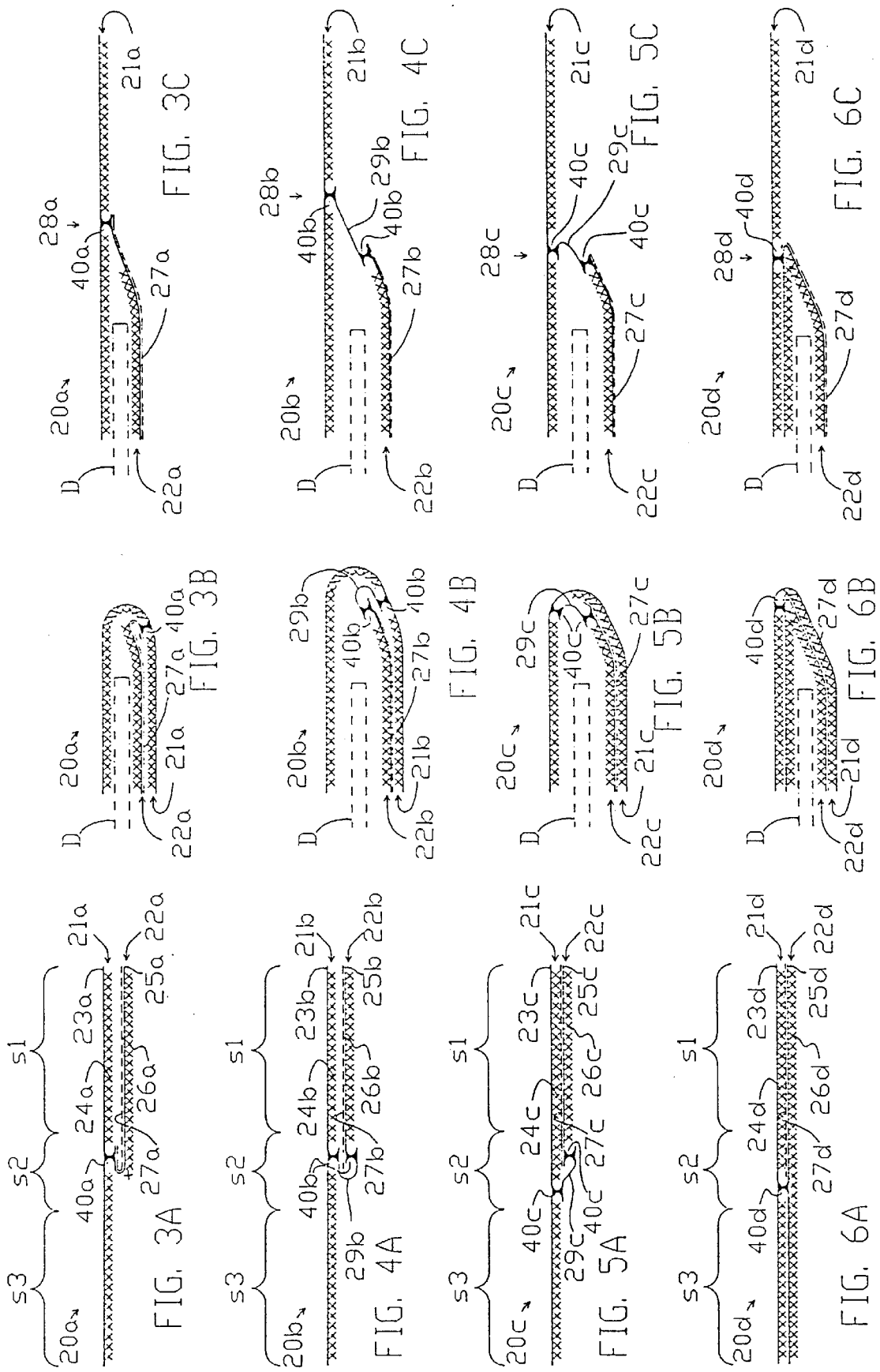

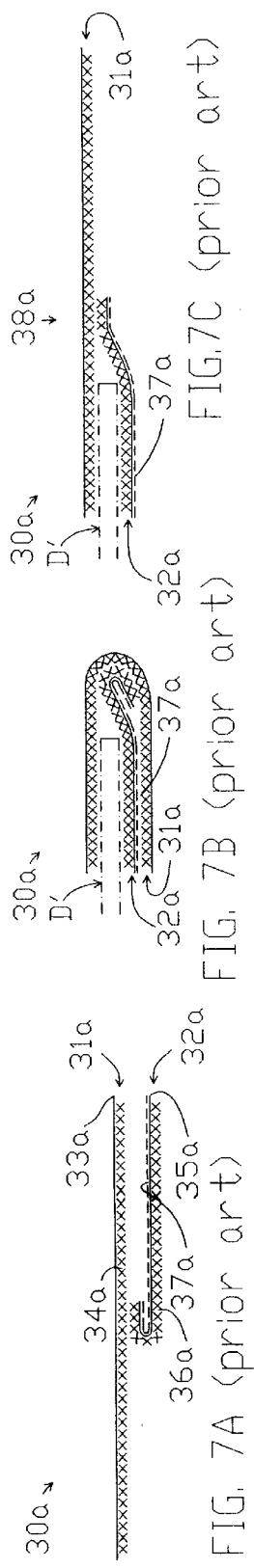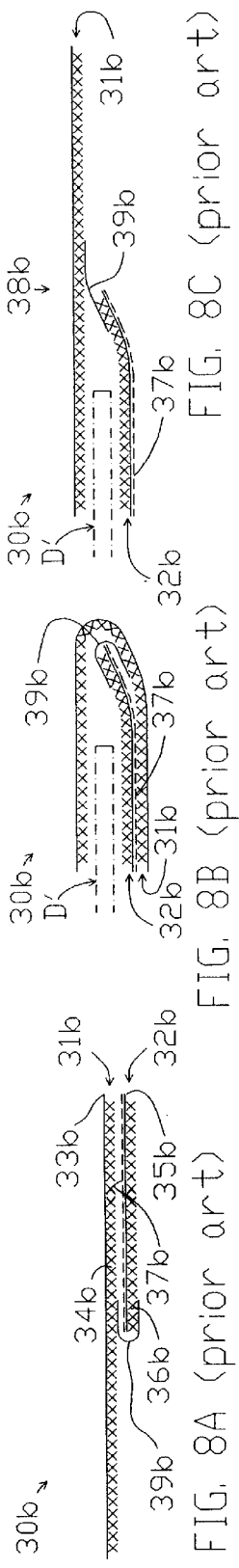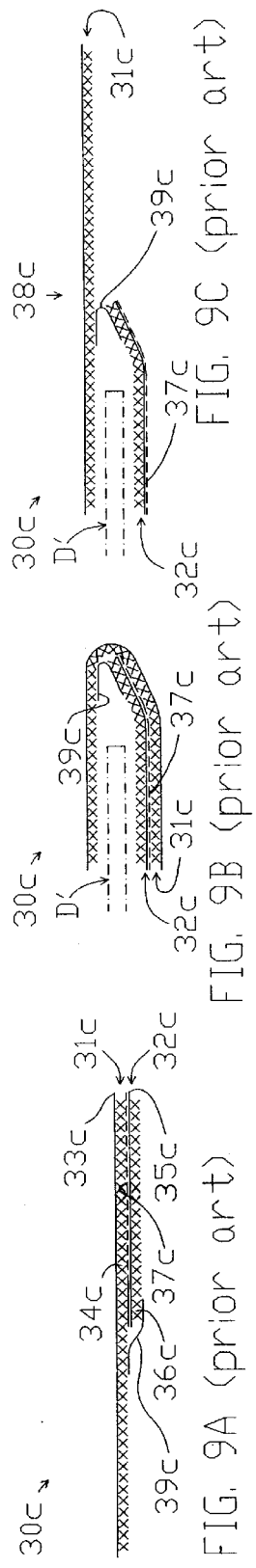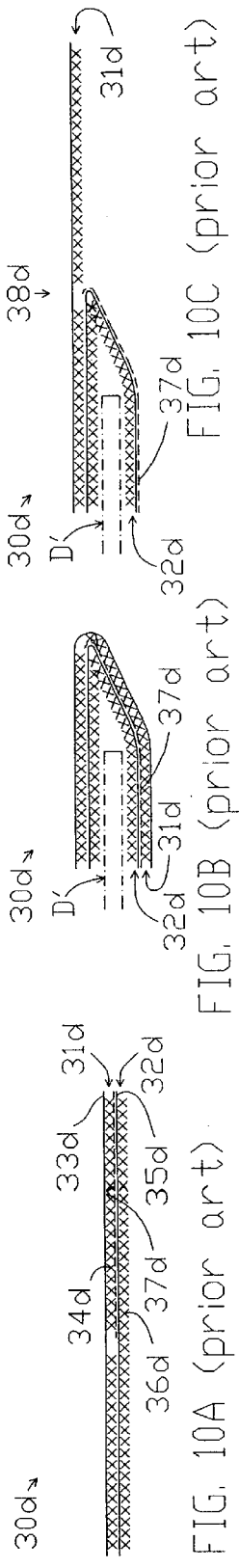

DIAPER FASTENING SYSTEM USING WELDED BRANCHING TYPE TABS

This is a continuation of application Ser. No. 08/325,988, filed Oct. 19, 1994, now abandoned.

This invention relates to taping systems for baby diapers and adult incontinence diapers, and more particularly to such systems wherein the diaper fastening tabs are each formed of minimally two distinctive tapes, commonly referred to fastening tape and release tape, to form tabs of the branching configuration type.

BACKGROUND OF THE INVENTION

Tapes of this general kind are combined in long lengths to provide rolls of diaper tab stock. A diaper manufacturer then dispenses and transversely severs the combined tapes in a sequential manner to form individual diaper tabs and apply them to the edges of diapers being manufactured. This operation forms the permanent "factory" joint between each individual refastenable tab and its associated diaper. When the tab is used to fasten the diaper on a user, the tab's free end is deployed for adhesive fastening directly to another part of the diaper, or to a reinforcing tape (also called a target tape or a landing zone tape) carried on such other part of the diaper. Fastening establishes a temporary "user" joint between the tab and such other part of the diaper.

When applied to a diaper, the fastening tape portion of the tab is generally folded around the diaper edge in a storage position, with the free end of the fastening tape portion carried on a release coating provided on the outside of the release tape portion of the tab. The free end of the fastening tape portion is lifted from the release coating to deploy the tab for fastening. In this deployed condition of the tab, the fastening tape portion extends from its distal end back past the edge of the diaper and is adhesively anchored to the backsheet of polyethylene or the like at the outside face of the diaper. Beyond the diaper edge, the release tape portion of the tab is joined to the fastening tape portion at a branching point. From this branching point, the release tape portion of the tab extends over and is adhesively anchored to the facesheet of moisture-pervious nonwoven fabric or the like at the inside face of the diaper. Tabs of this branching configuration type are of several different sub-types, including direct Y-bond, Y-bond junction, peel junction, and Adam (an acronym derived from "Area Divarication Adhesive Means", the title of Reed et al. U.S. Pat. No. 3,833,456 of common assignee, now expired). These various sub-types are referred to below in more detail.

The bond between the fastening tape and release tape portions of the tab at the tab's branching point strongly contributes to the distribution and absorption of tab tension forces imposed at the factory joint of the tab when the product is in use. If the bond at the branching point yields or fails, these forces are not properly distributed, and can destroy the relatively weak elements of the diaper to which the tab is attached at its factory joint, i.e., the thin backsheet of polyethylene or the like at the outside face of the diaper and the thin facesheet of moisture-pervious unwoven fabric or the like at the inside face.

BRIEF DESCRIPTION OF THE INVENTION

In some applications, the fastener tabs of diaper closure systems require so-called "repositionable" adhesive, exhibiting significantly lower peel strength values than other perhaps more conventional "permanent" adhesives. The lower peel strength allows the user joint end of the tab to be removable from weak surfaces such as polyethylene backsheet or from non-release-coated reinforcement tapes (also called target tapes or landing zone tapes) on the diaper backsheet, without destruction or tearing. Since the same adhesive is usually part of the fastening tape portion/release tape portion bond at the tab's branching point, the adhesive may there exhibit the same relatively low peel force resistance and cause the diaper system to fail. In such application, the present invention assures an ultra high permanent bond between fastening tape and release tape portions even though the adhesive must satisfy a different and inconsistent priority providing relatively easy release to thereby accomplish controlled adhesion.

However the invention is not limited to such particular application, but is generally useful to give ultra-high bond strength at the branching point between fastening tape and release tape portions of the diaper tab in such manner as to allow proper distribution and absorption of tab tension forces imposed at the factory joint of the tab when the product is in use.

The invention involves the provision of a welded joinder at the branching point between the fastening tape and release tape portions of the tab, the welded joinder being free of the diaper. The welded joinder comprises a direct weld between the substrates of the fastening tape and release tape portions, or welds between each of those two substrates and an intermediate junction substrate. The result is ultra-high strength at the branching point, strength approaching or equalling the break strength of the substrate material itself. The features and advantages of the invention will be more fully understood from the more detailed description given below.

PRIOR ART PATENTS

U.S. Pat. No. 5,176,670 to Roessler shows a hook-and-loop type fastener for diapers. The fastener comprises a long fastening tape and a second short tape. The two tapes are attached to opposite faces of the diaper at the factory joint. FIG. 5, taken together with col. 6, lines 6–13 are part of the disclosure. If this is taken to refer to heat bonding of sonic bonding at the bonded areas indicated by the dots in the drawing (applicants do not admit the correctness of such interpretation), such would comprise a welding of each tape to the diaper, as well as a weld between the tapes. The weld between the tapes would not be free of the diaper but would extend thereto, and would not establish a diaper-free weld joinder at the branching point of the tab. Because the bond between the tab tapes would not be independent of the diaper margin layers, the tension on the tape would not be distributed evenly to the inner and outer sides of the diaper. Since the weldment between the tapes and one side of the diaper margin would be continuous, the welding would have to be done at the diaper manufacturing site. Furthermore, as above mentioned, the tab is not an adhesive fastener, but a loop-and-hook type fastener.

U.S. Pat. No. 5,288,546 to Roessler discloses an adhesive diaper tab in which there may be a sonic bond between the outer end of the fastening tape and a fingerlift tape. See column 16, lines 41–47.

U.S. Pat. No. 5,053,028 to Zola discloses fastening the inboard end of a hook-and-loop type diaper tab between the inner and outer diaper margins by sonic bonding. See column 8, lines 50–54. (Roessler '670 contains similar showings in FIGS. 7–9.)

U.S. Pat. No. 5,147,347 to Haang mentions fastening the inboard end of an adhesive diaper tab by sonic bonds. See column 7, lines 58–62.

DESCRIPTION OF THE DRAWINGS

In the drawings, FIGS. 3A–3C are diagrammatic cross-sections of a direct Y-bond tab embodying the invention. FIGS. 3A' and 3C' correspond to FIGS. 3A and 3C and show a variant form of direct Y-bond tab embodying the invention (FIG. 3C being only fragmentary). FIGS. 4A–4C are diagrammatic cross-sections of a Y-bond junction tab embodying the invention. FIGS. 5A–5C are diagrammatic cross-sections of a peel junction tab embodying the invention. FIGS. 6A–6C are diagrammatic cross-sections of an Adam tab embodying the invention. The "A" drawing in each series shows a cross-section of an individual tab before it is applied around a diaper edge. (The "A" drawing in each drawing series may also be regarded as showing a cross section of the tape stock for the tab, with fastening tape, release tape, and junction (if any) assembled in preparation for severing into individual tabs.) The "B" drawing in each series shows the configuration of the tab as applied to the diaper edge, as taken on the plane of line B—B in FIG. 1. Such may be referred to as the storage configuration. The "C" drawing in each series shows the tab in fastening configuration wherein the free end of the tab's fastening tape portion is deployed for attachment to another part of the diaper, as taken on the plane of line C—C in FIG. 1. FIGS. 7A–7C, 8A–8C, 9A–9C, and 10A–10C are diagrammatic cross-sections showing prior-art branching configuration tabs of, respectively, the direct Y-bond, junction Y-bond, peel junction, and Adam sub-types, and are included for purposes of comparison, respectively, to FIGS. 3A–3C, 4A–4C, 5A–5C, and 6A–6C. The "B" and "C" drawings of each of these prior-art series are as taken on the planes of lines B'—B' and C'—C' in FIG. 2.

DETAILED DESCRIPTION OF THE INVENTION

Figure 1:
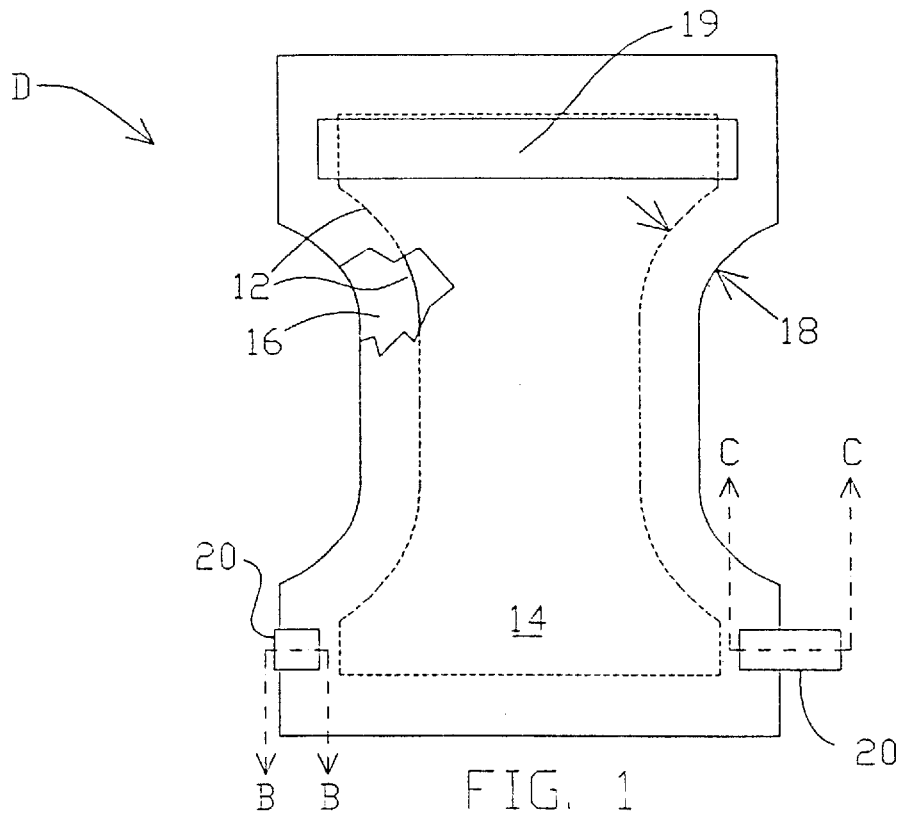
FIG. 1 is schematic sketch of novel combination of diaper with novel fastening tabs, embodying the invention, viewed from the moisture-impervious backsheet side of the diaper, but partly broken away to reveal the moisture-pervious facesheet of the diaper.

In FIG. 1, a diaper D includes a batt 12 of water-absorbent material encased between a moisture-impervious backsheet 14 of polyethylene or the like and a moisture-pervious facesheet 16 of unwoven fabric or the like. The sheets 14 and 16 extend beyond the batt 12 to form the marginal portion 18 around the diaper where the sheets 14 and 16 may contact each other. The diaper is shaped as shown to fit an infant. When worn, the backsheet is on the exterior and the facesheet is on the inside against the infant's skin.

The diaper 10 is provided with tab fasteners 20 at its side edges. These tabs are of the branching configuration type but are of novel construction to be described below. As seen in FIG. 1, the left tab fastener 20 is in storage position and the right tab fastener 20 is deployed for fastening. These tab fasteners may extend only over the marginal portion 18 of the diaper, as shown, or they may also extend over a small portion of the batt 12. A reinforcing tape 19 (also called a target tape or landing zone tape) may be applied to the backsheet 14 at the outside front waist portion of the diaper.

Each tab 20 is fastened by drawing its fastening tape portion over the associated end of the reinforcing tape 19 and pressing the fastening tape portion onto the reinforcing tape to releasably adhere the two. The further the latter is drawn over the former, the tighter the fit of the diaper. If no reinforcing tape is used, the fastening tape portions of the tabs are drawn over the same regions of the diaper as are occupied by the reinforcing tape in FIG. 1, and are then applied directly to the backsheet 14 with the intent of releasably adhering the two.

Sub-Types of Tab Fasteners of the Branching Configuration Type

Figure 2:
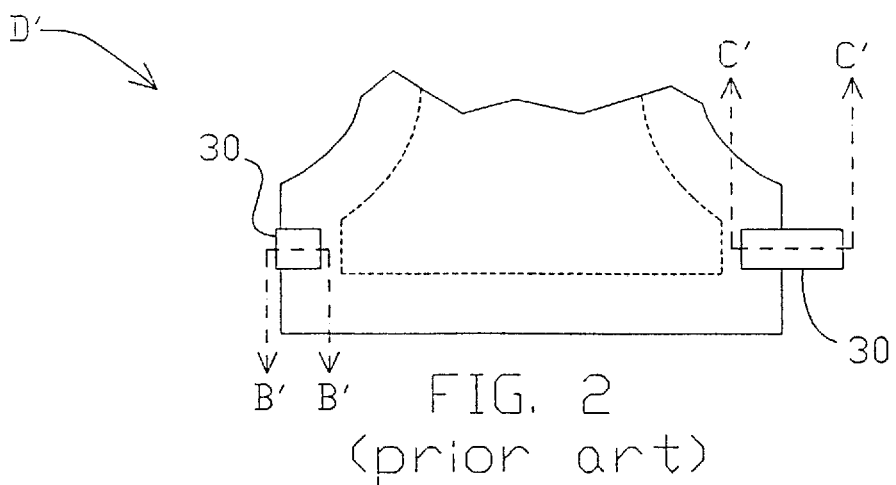
FIG. 2 is a sketch similar to FIG. 1, but fragmentary, showing a prior-art combination of diaper with prior-art fastening tabs.

To enable the operation and scope of the present invention to be most readily understood, four sub-types of tab fasteners of the branching configuration type will now be described in detail. A pair of prior-art tab fasteners 30 are shown in FIG. 2; the left tab fastener 30 is in storage position and the right tab fastener 30 is deployed for fastening. The tab fasteners 30 are of the branching configuration type and represent any one of the sub-types shown in FIGS. 7A–7C, 8A–8C, 9A–9C, and 10A–10C, including respectively direct Y-bond tab 30a, junction Y-bond tab 30b, peel junction tab 30c and Adam tab 30d.

Each of the tab fasteners 30a, 30b, 30c, and 30d has a fastening tape portion 31a, 31b, 31c, or 31d, and each also has a release tape portion 32a, 32b, 32c, or 32d. The fastening tape portion of each tab fastener includes a fastening tape substrate 33a, 33b, 33c, or 33d. The fastening tape portion of each tab fastener also includes fastening tape adhesive 34a, 34b, 34c, or 34d. The release tape portion of each tab fastener includes a release tape substrate 35a, 35b, 35c, or 35d. The release tape portion of each tab fastener also includes release tape adhesive 36a, 36c, 36c, or 36d. Each release tape portion further includes deployment-release coat or lacquer 37a, 37b, 37c, or 37d.

The tab 30a, 30b, 30c or 30d may be severed from the off-feed of a stock roll (not shown) comprising a combination of fastening tape and release tape. To enable the roll of stock to be self-wound without the use of separate release liner, an unwind-release coat (not shown) may be coated over the entire exposed surface of the fastening tape substrate 33a, 33b, 33c or 33d (the top surface as seen in the drawings). This coating is omitted from the drawings for purposes of clarity.

Upon severance and prior to application to the edge of the diaper D', the configuration of the tab is generally as shown in FIG. 7A, 8A, 9A, or 10A (but with the just-mentioned unwind-release coat). The tab 30a, 30b, 30c or 30d is then wrapped around the edge of the diaper D' to grip both sides thereof, as shown in FIG. 7B, 8B, 9B, or 10B, with the free-able end of the fastening tape portion carried on deployment-release coat 37a, 37b, 37c, or 37d. When the diaper is to be fastened, the freeable end of the fastening tape portion 31a, 31b, 31c, or 31d is lifted from its associated deployment-release coat to free it and deploy the tab for fastening, as shown in FIG. 7C, 8C, 9C, or 10C.

In this deployed condition of the tab, the fastening tape portion extends from its distal end back past the edge of the diaper D' and is adhesively anchored to the backsheet of polyethylene or the like at the marginal portion of the diaper and at the outside face of the diaper (being either directly adhesively anchored as in the configurations of FIGS. 7–9 or indirectly adhesively anchored via the non-release-coated end of the release tape portion, as in the configuration of FIG. 10). At or just outwardly beyond the diaper edge, the release tape portion 32a, 32b, 32c, or 32d of the tab is joined to its associated fastening tape portion at a branching point 38a, 38b, 38c, or 38d. From this branching point, the release tape portion also extends back past the edge of the diaper and is adhesively anchored to the inside face of the diaper at the marginal portion of the diaper.

The bond between the fastening tape portion and the release tape portion of the tab at the branching point strongly contributes to the distribution and proper absorption of tab tension forces that are imposed on the factory joint while the fastened diaper is worn. These forces, when not properly distributed, can easily destroy relatively weak elements, for example polyethylene backsheet, to which the tab fastener is attached.

The direct Y-bond configuration of tab 30a (FIG. 7) is generally perceived as the strongest combination of fastening tape and release tape. The Y-bond junction configuration of tab 30b (FIG. 8) is similar but uses an additional narrow strip of tape to provide the junction substrate 39b. In tabs 30a and 30b, fastener and release tape portions are combined, directly or via the junction, over a few millimeters of the width of the tapes (length of the tab). As a result, each of tabs 30a or 30b provides a branching point 38a (FIG. 7) or 38b (FIG. 8) from which the tension forces, generated while the fastened diaper is worn, are distributed evenly to the inner and outer sides of the diaper at the factory joint. The tape-to-tape bonds at the branching points can only be separated by overcoming the shear strengths of the bonds, which are generally higher (often much higher than their peel strengths.

The peel junction configuration of tab 30c (FIG. 9) also uses an additional narrow tape to provide a junction substrate, 39c, at the branching point 38c. From this branching point, the tension forces, generated while the fastened diaper is worn, are distributed evenly to the inner and outer sides of the diaper at the factory joint. In the Adam configuration of tab 30d (FIGS. 10A–10C), when the fastener is affixed to the diaper at the diaper factory, the release tape portion 32d (as well as the fastening tape portion 31d) extends around the diaper edge from one side of the diaper to the other, so that the fastening tape portion 31d is supported indirectly on the associated face of the diaper margin, said indirect support being through the part of the underlying release tape portion 32d that is adhered to the diaper on that same face. From the branching point 38d, the tension forces, generated while the fastened diaper is worn, are distributed evenly to the inner and outer sides of the diaper at the factory joint.

The fastening tape portions 31a, 31b, 31c and 31d of the tabs described all extend around the diaper edge from one side of the diaper to the other when the fastener is affixed to the diaper at the factory. The fastening tape substrates 33a, 33b, 33c and 33d all extend around the edge without interruption, as do the fastening tape adhesives 34a, 34b, and 34c. However, the fastening tape adhesive 34d of the Adam type fastener (FIGS. 10A–10C) is preferably interrupted by a small gap, as shown.

The peel junction configuration of tab 30c (FIGS. 9A–9C) and the Adam configuration of tab 30d (FIGS. 10A–10C) are perceived as weaker than the configurations of FIGS. 7A–7C and FIGS. 8A–8C, since the configurations of FIGS. 9A–9C and FIGS. 10A–10C experience peeling action when subjected to the tension forces generated while the fastened diaper is worn, whereas the configurations of FIGS. 7A–7C and FIGS. 8A–8C only experience shearing action when subjected to such tension forces. This may be most readily understood by comparing the branching points 38a and 38b of FIGS. 7C and 8C on the one hand with branching points 38c and 38d of FIGS. 9C and 10C on the other. (It should be remembered that the tabs are diagrammatically shown in these figures as deployed for fastening, but prior to being fastened and therefore prior to being subjected to tension forces. Therefore, as shown, the tabs have yet to be stressed and stretched by tension forces resulting from, say, squirming of an infant. It will be understood that such stressing and stretching will contribute to peeling action at junctions 38c and 38d. In the case of the Adam construction shown in FIG. 10, in tensioned condition, the point of forking, i.e.. the branching point, tends to form at the point between the fastening tape adhesive 34d and the release tape substrate 35d where the deployment release coat 37d terminates. For analogous illustrations of such a condition where "area divarication" occurs, see FIG. 3a and column 5, lines 5–17 of Richman et al. U.S. Pat. No. 4,020,842 of common assignee, now newly expired, and FIG. 6 of Richman U.S. Pat. No. 4,050,121, the disclosures of which are incorporated herein by reference.)

The Adam configuration of tab 30d (FIG. 10) has been in commercial use for many years because it is suitable to low cost production and high speed dispensing. However, since the Adam configuration is subject to peeling action, as above described, a particular problem is presented if the Adam configuration is used in diaper closure systems requiring a so-called "repositionable" adhesive which exhibits relatively low peel strength values. As previously mentioned, the relatively low peel strength allows the user joint end of the tab to be removable from weak surfaces such as polyethylene backsheet or from non-release-coated reinforcement tapes (also called target tapes or landing zone tapes) on the diaper backsheet, without destruction or tearing. Since the same adhesive is usually part of the fastening tape portion/release tape portion bond at the tab's branching point, the adhesive there exhibits the same relatively low peel force resistance and failure of the diaper fastening system may result. It is not always possible to balance the conflicting requirements of (1) easy or "controlled" release needed for opening or repositioning of the fastened diaper tab and (2) sufficient peel resistance to give adequate strength at the branching point of the Y-configuration tab. The same observations apply to the peel junction configuration of FIG. 9.

For completeness, another two-tape tab of the prior art (not shown) may be mentioned. It is referred to as a no-bond tab. It comprises simply a fastening tape portion applied to the backsheet of the diaper and a release tape portion applied to the facesheet, with no connection between the two. In the storage position, the facesheet is folded around the edge of the diaper onto the release sheet. In the deployed position, the fastening tape portion is unfolded from around the diaper edge and extended, at which point the two tape portions are disassociated. The configuration would appear similar to that of FIGS. 7B and 7C but without any contact between the tape portions except for support of the fastening tape portion on the release coating of the release tape portion in the storage position.

While the present invention is directed most specifically to tabs of the peel junction and Adam types, it can be applied to provide improved diaper tabs of any of the types discussed above.

The Tab Fasteners of the Present Invention

The tabs 20 of FIG. 1 are tabs of the branching configuration type which embody the invention, and represent any one of the sub-types shown in FIGS. 3–6, including direct Y-bond tab 20a, junction Y-bond tab 20b, peel junction tab 20c and Adam tab 20d.

Each of the tab fasteners 20a, 20b, 20c, and 20d has a fastening tape portion 21a, 21b, 21c, or 21d, and each also has a release tape portion 22a, 22b, 22c, or 22d. The fastening tape portion of each tab fastener includes a fastening tape substrate 23a, 23b, 23c, or 23d. The fastening tape portion of each tab fastener also includes fastening tape adhesive 24a, 24b, 24c, or 24d. The release tape portion of each tab fastener includes a release tape substrate 25a, 25b, 25c, or 25d. The release tape portion of each tab fastener also includes release tape adhesive 26a, 26c, 26c, or 26d. Each release tape portion further includes deployment-release coat or lacquer 27a, 27b, 27c, or 27d.

Each of the tab fasteners has, with respect to its length direction, a first terminal segment s1, a central segment s2, and a second terminal segments s3. Each release tape portion 22a, 22b, 22c, or 22d extends along at least the first terminal segment s1 and part of the central segment s2 (the release tape portion 22d extends along all three segments, s1, s2 and s3). Each release tape portion is adhesively anchored to the inside face of the diaper to define one part of the factory joint between the tab and the diaper. Each fastening tape portion 21a, 22a, 23a, or 24a overlies its corresponding release tape portion and extends along all three segments, s1, s2 and s3. Each fastening tape portion is adhesively anchored, either directly or through the release tape portion 22d in the case of the fastening tape 21d, to the outside face of the diaper to define the other part of the factory joint between the tab and the diaper.

As in the tab of the prior art, the tab 20a, 20b, 20c or 20d may be severed from the off-feed of a stock roll (not shown) comprising a combination of fastening tape and release tape. To enable the roll of stock to be self-wound without the use of separate release liner, an unwind-release coat (not shown) may be coated over the entire exposed surface of the fastening tape substrate 23a, 23b, 23c, or 23d (the top surface as seen in the drawings. This coating is omitted from the drawings for purposes of clarity.

Upon severance and prior to application to the edge of the diaper D, the configuration of the tab is generally as shown in FIG. 3A, 4A, 5A, or 6A (but with the just-mentioned unwind-release coat). The tab 20a, 20b, 20c or 20d is then wrapped around the edge of the diaper D to grip both sides thereof, as shown in FIG. 3B, 4B, 5B, or 6B, with the free-able end of the fastening tape portion 21a, 21b, 21c, or 21d carried on deployment-release coat 27a, 27b, 27c, or 27d. When the diaper is to be fastened, the free-able end of the fastening tape portion 21a, 21b, 21c, or 21d is lifted from its associated deployment-release coating to free it and deploy the tab for fastening, as shown in FIG. 3C, 4C, 5C, or 6C.

In this deployed condition of the tab, the fastening tape portion extends from its distal end back past the edge of the diaper D and, as previously indicated, is adhesively anchored to the diaper at its outside face; that is, the fastening tape portion is adhesively anchored to the backsheet of polyethylene or the like at the marginal portion of the diaper and at the outside face of the diaper (being either directly adhesively anchored to the backsheet as in the configurations of FIGS. 3–5, or indirectly adhesively anchored to the backsheet via the non-release-coated end of the release tape portion, as in the configuration of FIGS. 6A–6C). Outwardly of the diaper edge, the release tape portion 22a, 22b, 22c, or 22d of the tab is joined to its associated fastening tape portion at a branching point 28a, 28b, 28c, or 28d. From this branching point, the release tape portion also extends back past the edge of the diaper and is adhesively anchored to the inside face of the diaper at the marginal portion of the diaper.

As in the fasteners 30a, 30b, 30c and 30d, the fastening tape portions (21a, 21b, 21c and 21d) of the fasteners 20a, 20b, 20c and 20d all extend around the diaper edge from one side of the diaper to the other when the fastener is affixed to the diaper at the diaper factory. As in the Adam type fastener 30d of the prior art, in the preferred Adam type fastener 20d of the present invention, when the fastener is affixed to the diaper at the factory, the fastening tape adhesive (24d) is interrupted by a small gap. However, in the practice of the present invention in the manufacture of fasteners other than those of the Adam type, the fastening tape adhesives 24a, 24b, and 24c are preferably similarly interrupted by small gaps, as shown, to allow for welding procedures similar to those to be described below.

Tab fasteners 20b and 20c respectively utilize junction substrates 29b and 29c. The branching configurations of the tab fasteners 20a, 20b, 20c and 20d will be seen to generally correspond to those of the tab fasteners 30a, 30b, 30c and 30d. However, tab fasteners 20a, 20b, 20c and 20d each include welded joinders between their fastening tape substrate and release tape substrate at their branching point. The welded joinder which joins fastening tape substrate 23a and release tape substrate 25a comprises a single weld 40a. The welded joinder which joins fastening tape substrate 23b and release tape substrate 25 comprises the two welds 40b and the junction substrate 29b. The welded joinder which joins fastening tape substrate 23c and release tape substrate 25c comprises the two welds 40c and the junction substrate 29c. The welded joinder which joins fastening tape substrate 23d and release tape substrate 25d comprises a single weld 40d.

Welded joinders comprising a single weld, such as the welds 40a and 40d, are simpler to make than those comprising two welds and a junction substrate. A presently preferred construction is of the tab 20d shown in FIGS. 6A–6C. Presently preferred practice for forming this construction will now be described. In this description, it will be understood that references are to the construction as seen in FIG. 6A, interpreted however as applying not to discrete diaper tabs, but to the continuous lengths of diaper tab stock as formed, coated and combined by the manufacturer of the diaper tap stock.

In presently preferred practice, the manufacturer of the diaper tab stock coats one face of the fastening tape substrate with an unwind release coat (not shown), pattern coats the other face with the fastening tape adhesive, leaving the small gap shown (which may be, say 6 mm wide), pattern coats part of the width of one face of the release tape substrate with the deployment-release coat, then combines that face of the release tape substrate against the fastening tape adhesive before the release tape substrate has received its release coat adhesive, then applies the sonotrode of a sonic welder directly to the outside or unwind-release-coated face (the top or outside face as seen in FIG. 6A) of the fastening tape substrate at the center of the small adhesive gap while supporting the release tape substrate (which is as yet uncoated with release tape adhesive) with a stainless steel or ceramic back-up roll. Following welding, the exposed face of the release tape substrate is coated with the release tape adhesive and the stock is then wound into a self-wound roll.

The weld is continuous and extends, of course, along the line direction of the coating and laminating line, and therefore across the width direction of diaper tabs to be cut from the stock.

In tests using polypropylene of a thickness of 60–120 microns, the applied sonotrode was operated at amplitudes between 25 and 60 microns and placed at a distance from the web equal to half the amplitude (between 12.5 and 30 microns). Good welding was obtained at speeds between 30 and 90 m/min. at a frequency of 36 kHz. Other frequencies (e.g. 25 kHz) are possible but require other settings.

The welding equipment used in the tests was generator Model SG25-500-36 kHz with convertor Model SE-26/20-36 kHz manufactured by Telsonic Ultrasonics AG, Bronschhofen, Switzerland.

All these welded joinders are free of the diaper D in the sense that there is no weldment between them and any part of the diaper; rather they are tied to the diaper only by unsupported lengths of adhesive-coated fastening tape substrate and/or release tape substrate. The tension forces generated while the diaper is worn are therefore distributed from the branching point of each of these fasteners evenly to the inner and outer sides of the diaper at the factory joint, while at the same time the bond between the fastening tape substrate and release tape substrate is equal to the strength of the substrate material itself.

In respect of the direct Y-bond tab 20a and junction Y-bond tab 20b, the provision of diaper-free welded joinders at the branching point according to the invention means that even distribution of tension forces is maintained while improving the substrate-to-substrate bond to the point where it can only be separated by overcoming the break strength of the substrate material itself.

In respect of the peel junction tab 20c and Adam tab 30d, the provision of diaper-free welded joinders at the branching point means the same. Furthermore, since the Adam configuration (and the peel junction configuration) are subject to peeling action, as above described, the invention is particularly advantageous if the Adam configuration (or the peel junction configuration) is used in diaper closure systems requiring a so-called "repositionable" adhesive which exhibits relatively low peel strength values. As previously mentioned, the relatively low peel strength allows the user joint end of the tab to be removable from weak surfaces such as polyethylene backsheet or from non-release-coated reinforcement tapes (also called target tapes or landing zone tapes) on the diaper backsheet, without destruction or tearing. Heretofore, since the same adhesive is usually part of the fastening tape portion/release tape portion bond at the tab's branching point, the adhesive there exhibits the same relatively low peel force resistance and failure of the diaper fastening system may result. In such application, the present invention assures an ultra high permanent bond and peel strength at the branching point between fastening tape and release tape portions, allowing the adhesive to be uncompromisingly selected to meet a different and formerly inconsistent priority—that of providing relatively easy release to thereby accomplish controlled adhesion.

It has been known to use separate side-by-side coatings of different adhesives instead of providing the same adhesive as the fastening tape adhesive at all areas on the fastening tape substrate. In such constructions, one adhesive provides the bond at the branching point and the other provides the releasable bond to another part of the diaper. However, such constructions require pattern coating the two different adhesives beside each other on the fastening tape substrate and are not as simple as the present invention.

Figure 3A:
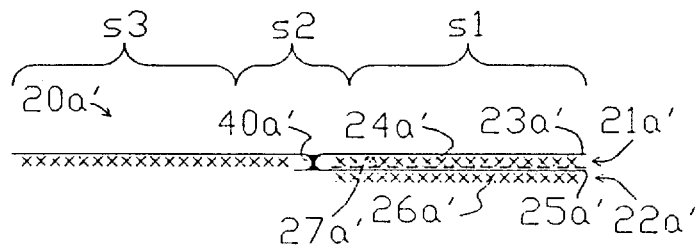
Figure 3C:
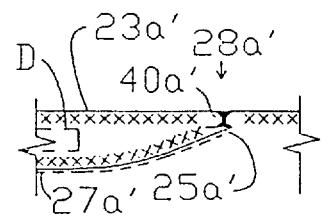

For completeness, a variant form of direct Y-bond tab is shown in FIGS. 3A' and 3C' which correspond to FIGS. 3A and 3C. Like the previously described tab fasteners, the tab 20a' shown in FIGS. 3A' and 3C' has, with respect to its length direction, a first terminal segment s1, a central segment s2, and a second terminal segments s3. The tab 20a' has a fastening tape portion 21a', a release tape portion 22a', a fastening tape substrate 23a', a fastening tape adhesive 24a', a release tape substrate 25a', a release tape adhesive 26a', a release coat 27a', a branching point 28a', and a weld 40a'. The tab 20a' differs from the tab 20a in that the weld 40a' of tab 20a' is joined to the upper face of the release tape substrate 25a' (the face opposite from the face that receives the release tape adhesive 26a'), while the weld 40a of the tab 20a is joined to the backfolded lower face of the release tape substrate 25a (the same face that receives the release tape adhesive 26a). The tab 20a' is generally similar to the tab 20a in concept and operation, as will be readily understood. In some circumstances, the tab 20a' may be found preferable in that its elements may be more conveniently positioned to carry out the welding step during manufacture.

It should be evident that this disclosure is by way of example, and that various changes may be made by adding, modifying or eliminating details without departing from the fair scope of the teaching contained in this disclosure. The invention therefore is not limited to particular details of this disclosure except to the extent that the following claims are necessarily so limited.

What is claimed is:

1. In a disposable diaper provided with a tab fastening system including a tab fastener of the Y-configuration type, said tab fastener having length, width and thickness directions and dimensions, and further having, with respect to its length direction, first and second terminal segments and a central segment between the terminal segments, the tab fastener comprising first and second tab portions each comprising a separate planar resinous film tape substrate having a resinous film thickness and a layer of adhesive supported on the substrate, said first tab portion comprising a release tape portion extending along said first terminal segment and also along at least a portion of said central segment, said second tab portion comprising a fastening tape portion overlying said release tape portion and extending along said first terminal segment and said central segment and said second terminal segment, a release coating between said fastening tape portion and said release tape portion along said first terminal segment of said tab whereby said fastening tape portion is releasable from said release tape portion along said first terminal segment for freeing and deployment of the end of said fastening tape portion associated with said first terminal segment, the improvement wherein said separate substrates of said first and second tab portions are joined by a welded joinder of the resinous films of said substrates, said films being disposed in superposed relationship at said welded joinder, said welded joinder extending across said width direction of said tab fastener at said central segment, said welded joinder being free of connection with said diaper and the strength of said joinder being independent of the bonding strength of the adhesive of said adhesive layers, and said welded joinder having a break strength substantially as high as a break strength of the substrates.

2. A disposable diaper as in claim 1, said welded joinder comprising a weld directly between said resinous films of said substrates.

3. A disposable diaper as in claim 1, a junction strip of resinous film material extending across said width direction of said tab fastener at said central segment, said welded joinder comprising (a) said resinous film of said junction strip, (b) a first weld between said resinous film of said junction strip and said resinous film of said substrate of said first tab portion, and (c) a second weld between said resinous film of said junction strip and said resinous film of said substrate of said second tab portion.

4. A disposable diaper as in claim 2, said tab of the Y-configuration type being of the sub-type wherein said first tab portion comprising the release tape portion extends along said second terminal segment as well as along said first terminal segment and said central segment.

5. A disposable diaper as in claim 1, wherein said welded joinder extends in said width direction of said tab fastener entirely across said width dimension of said tab fastener.

* * * * *